(12) United States Patent
Sulprizio

(10) Patent No.: US 6,942,704 B2
(45) Date of Patent: Sep. 13, 2005

(54) PROSTHETIC FOOT

(75) Inventor: Michael Scott Sulprizio, Gardnerville, NV (US)

(73) Assignee: S & L, Inc., Tacoma, WA (US)

( * ) Notice: Subject to any disclaimer, the term of this patent is extended or adjusted under 35 U.S.C. 154(b) by 57 days.

(21) Appl. No.: 10/651,699

(22) Filed: Aug. 29, 2003

(65) Prior Publication Data

US 2005/0049721 A1 Mar. 3, 2005

(51) Int. Cl.$^7$ .................................................. A61F 2/66
(52) U.S. Cl. ........................... 623/52; 623/53; 623/55
(58) Field of Search ............................ 623/47, 48, 49, 623/50, 51, 52, 53, 54, 55, 56

(56) References Cited

U.S. PATENT DOCUMENTS

| | | | |
|---|---|---|---|
| 292,800 | A | 2/1884 | Furrer |
| 1,319,471 | A | 10/1919 | Giebeler-Wanke |
| 2,470,480 | A | 5/1949 | Fogg |
| 2,475,372 | A | 7/1949 | Catranis |
| 4,364,128 | A | 12/1982 | Mummert |
| 4,822,363 | A | 4/1989 | Phillips |
| 5,037,444 | A | 8/1991 | Phillips |
| 5,116,384 | A | 5/1992 | Wilson et al. |
| 5,376,139 | A | 12/1994 | Pitkin |
| 5,387,246 | A | 2/1995 | Phillips |
| 5,443,528 | A | 8/1995 | Allen |
| 5,514,185 | A | 5/1996 | Phillips |
| 5,571,213 | A | 11/1996 | Allen |
| 5,593,457 | A | 1/1997 | Phillips |
| 5,653,768 | A | 8/1997 | Kania |
| 5,695,527 | A | 12/1997 | Allen |
| 5,766,265 | A | 6/1998 | Phillips |
| 5,944,760 | A | 8/1999 | Christensen |
| 5,976,191 | A | 11/1999 | Phillips |
| 6,019,795 | A | 2/2000 | Phillips |
| 6,099,572 | A | 8/2000 | Mosler et al. |
| 6,165,227 | A | 12/2000 | Phillips |
| 6,241,776 | B1 | 6/2001 | Christensen |
| 6,306,178 | B1 | 10/2001 | Kania et al. |
| 6,402,790 | B1 | 6/2002 | Celebi |
| 6,406,500 | B1 | 6/2002 | Phillips |
| 2002/0013628 | A1 | 1/2002 | Harris |
| 2002/0077706 | A1 | 6/2002 | Phillips |
| 2002/0143406 | A1 | 10/2002 | Townsend et al. |
| 2002/0143408 | A1 | 10/2002 | Townsend et al. |

FOREIGN PATENT DOCUMENTS

| | | |
|---|---|---|
| DE | 42 08 941 | 9/1993 |
| WO | WO 93/04645 | 3/1993 |

*Primary Examiner*—David H. Willse
*Assistant Examiner*—Javier G. Blanco
(74) *Attorney, Agent, or Firm*—Kelly Lowry & Kelley, LLP (57) ABSTRACT

A prosthetic foot including a ground-engaging base in the form of a generally planar and resiliently flexible foot bed which extends between two or more platforms to form one or more flexible hinges therebetween. The platforms include a toe platform, a mid-section platform and a heel platform. A support shank is disposed above the platforms so as to be generally positioned above an ankle area of the foot. A first spring extends from the toe platform to the support shank. A second spring extends from the support shank to the mid-section platform. A third spring extends from the support shank to the heel platform. Typically, the springs are curvilinear springs.

32 Claims, 7 Drawing Sheets

PROSTHETIC FOOT

BACKGROUND OF THE INVENTION

The present invention generally relates to prosthetic foot devices. More particularly, the present invention relates to a prosthetic foot having a ground-engaging base with at least one flexible hinge and a spring structure to simulate the performance of natural foot movement.

Many individuals have lost a limb for various reasons including war, accident, or disease. In most of these instances, these individuals are aided in their everyday lives by a prosthetic limb. The objective of prosthesis is to provide an artificial limb that simulates the function and natural feel of the replaced limb.

Artificial limbs and particularly prosthetic feet and legs have been known for centuries. The earliest were probably similar to the crude wooden "peg legs". These early devices enabled the user to stand and to walk awkwardly, usually with the additional aid of a crutch or cane. Over time, designers of artificial or prosthetic feet attempted to duplicate the appearance and function of a natural foot. The development of a functional and natural artificial foot has been limited only by material and imagination. Various types of foot and leg prosthetic devices are well-known in the prior art. Such devices generally include some form of attachment for coupling the device to the dorsal end of the limb and for extending to the ground to provide body support. Normally, the prosthetic device is strapped to the limb to keep the prosthetic device in place throughout the wearers normal motion, particularly when lifting the limb for walking and the like.

Many designs have attempted to copy the anatomy of the foot or simulate its action by replacing the bones and muscles with various mechanical components. Designers have attempted to closely approximate the action of natural foot by adding ball and socket ankle joints geometrically similar to a natural anatomical ankle. However, without all the muscles, tendons and cooperating bone structure of an anatomical foot, the anatomical type ankle joint is too unstable to be practical. Moreover, another problem with such configurations is the complexity of the several joints. There are numerous moving parts and joints subject to friction, wear, and failure.

Other designs have departed radically from mere anatomical copying and mechanical simulation by replacing the entire foot with an energy storage element such as a spring. Various prosthetic feet in the prior art have been designed with spring components and tend to store energy when the foot is placed on the ground and to releases it and provide a lift or thrust as the foot is removed from the ground again to aid in the patient's gait and propel the user forward.

However, no prosthetic foot in the prior art has been completely successful in approximating the performance and response of a natural foot. Those prior art prosthetic feet which did not utilize a spring-loaded heel experienced a lag or deadness after the user placed the heel on the ground and began to roll the foot forward during the gait cycle. This was due to the necessity of loading a spring in the toe section after the user's weight had been placed on the ground. The response and feel of a natural foot cannot be achieved unless the springs are loaded as the user's weight is placed on the ground rather than after. Other prior art prosthetic feet utilize a spring-loaded heel which operated on the spring separate from the springs in the toe section effectively stored energy in the heel, but were ineffective in transferring energy from the heel to the toe portion of the prosthetic foot as the foot rolled forward during the gait cycle. These devices still required separate loading of the spring in the toe section. As a result, the user noticed a distinct and unnatural lag or hesitation in rolling the foot forward during the gait cycle, giving the foot an unnatural feel and possibly causing an uneven stride.

One-piece spring devices experienced a lag or deadness after the patient placed the heel on the ground and began to roll forward because the spring design was not suited to absorb and store sufficient energy in the heel and then transfer it to the toe section, thus requiring the toe section to be loaded after the patient's weight had been placed on the ground. Such dead or flat spots are particularly noticeable when navigating steps or walking backwards. Oftentimes, users wearing a prosthetic foot would hang at least a portion of the prosthetic foot over the stair and then roll the foot over the stair in a leverage manner, similar to a teeter-tauter, to navigate the stair as the user descends.

Nearly all of the past designs have focused on the major aspect of the prosthetic foot, that is movement of the ankle or foot as it relates to walking or running. Very few designs have considered the workings of the toes or less conspicuous movements of the foot and ankle when the user navigates an incline, decline or uneven terrain. The prosthesis of the previous designs usually incorporate a unitary foot and toe platform that is incapable of such independent rotational movement or response. Thus, the users were required to dig the toe or heel into the decline or incline to provide sufficient stability to navigate the same. When experiencing uneven terrain, such as rocks, the prosthetic foot was unable to navigate such obstacles and often caused tension or even hyperflexion of the user's knee or hip.

Accordingly, there is a continuing need for an improved prosthetic foot which better simulates the fluid movement and natural gait of a real foot. Such a prosthetic foot should provide fluid movement without dead or flat spots. Such prosthetic foot should also conform to irregular surfaces, inclines and declines. Such prosthetic foot should not be very complex in design nor costly. The present invention fulfills these needs and provides other related advantages.

SUMMARY OF THE INVENTION

The present invention resides in a prosthetic foot which is simple in construction and durable yet provides a fluid movement without dead or flat spots so as to simulate the natural movement or gait of a foot. The prosthetic foot of the present invention also enables the user to walk stairs, inclined or declined surfaces, or even irregular surfaces.

The prosthetic foot includes a ground-engaging base having a toe platform, a mid-section platform and a heel platform. In one embodiment, the mid-section platform is defined by a forward portion of a unitary platform, and the heel platform is defined by a rear portion of the unitary platform. In a second embodiment, the platforms are separated from one another and spaced apart and generally aligned with one another.

Flexible hinges extend between the platforms. The flexible hinge preferably comprises a foot bed which is generally planar and resiliently flexible and which extends between lower surfaces of the two or more platforms.

A support shank is disposed above the platform so as to be generally positioned above an ankle area of the foot. A first spring extends from the toe platform to the support shank. A second spring extends from the support shank to the mid-section platform, and a third spring extends from the support shank to the heel platform. Typically, the first, second and third springs comprise curvilinear leaf springs. In a particularly preferred embodiment, the first and third springs extend from a front portion of the support shank to their respective platforms. The second spring extends from a back portion of the support shank to the mid-section platform.

The second spring may comprise a pair of springs extending from the support shank to a pair of mid-section platforms. In this embodiment, each second spring is disposed on opposite sides of the third spring such that the third spring can travel therebetween in response to forces applied to the foot, thus forming a flexible axis. Alternatively, the second curvilinear leaf spring includes an elongated slot adapted to receive the third curvilinear spring therethrough so as to permit the third spring to travel along at least a partial length of the second spring in response to such forces and also forming a flexible axis.

Another modification of the prosthetic foot of the present invention can comprise the use of two first springs, each spring extending from the support shank to a pair of laterally spaced toe platforms. Alternatively, the first curvilinear spring can include a forked end, each end being attached to the laterally spaced apart toe platforms. In such an embodiment, the foot bed may include a slit between the laterally spaced apart toe platforms to provide greater freedom of movement between the toe platforms.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings for purposes of illustration the present invention resides in a prosthetic foot device having design and using materials which result in a more natural and fluid foot movement.

Figures 1, 2:
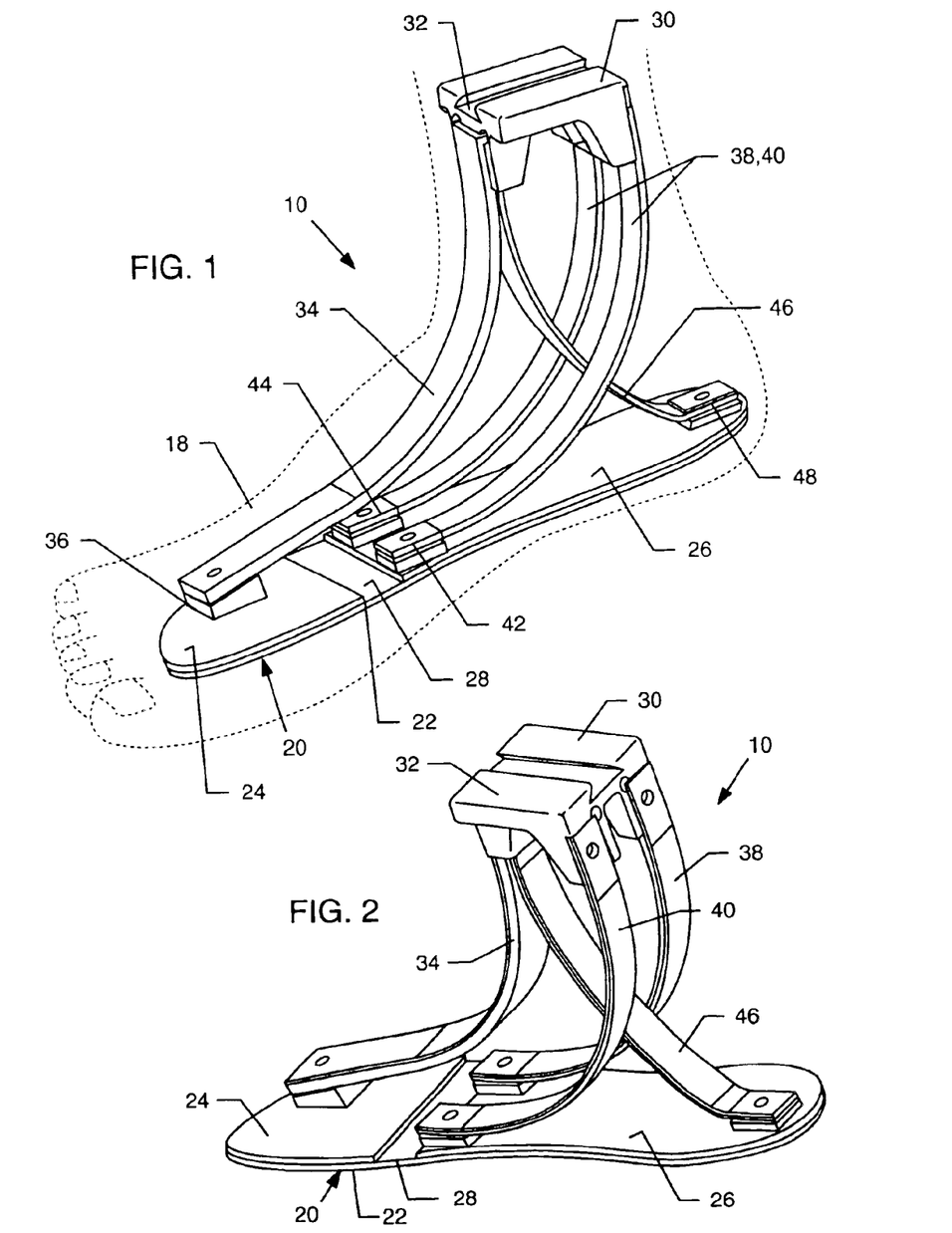
FIG. 1 is a perspective view of a prosthetic foot embodying the present invention, and covered with a foot encasement, illustrated in phantom.
FIG. 2 is a rear side perspective view of the prosthetic foot device of FIG. 1.

With reference now to FIGS. 1 and 2, a prosthetic foot 10 embodying the present invention is illustrated. The prosthetic foot device 10 is preferably encased within a rubber encasement 18 which resembles a foot and allows the user to wear shoes and otherwise provide the appearance of a natural foot, as is well-known in the art.

A ground-engaging base 20 is typically comprised of a generally planar and resiliently flexible foot bed 22. The foot bed 22 can be comprised of many materials, but it has been found that material such as a transmission belt is sufficiently durable and yet provides the characteristics desired by the present invention. However, any flexible material is contemplated by the present invention as comprising the foot bed 22.

In the embodiment illustrated in FIGS. 1 and 2, a first platform 24 is attached to the foot bed 22 in a toe portion of the foot. Preferably, the platform 24 is substantially rigid. A second platform 26 is spaced apart from the first platform 24 so that a flexible hinge 28 is formed between the two platforms 24 and 26. The second platform 26 is elongated and extends from a mid-section of the foot to a heel portion of the foot.

A support shank 30 is disposed above the ground-engaging base 20 and positioned so as to be above the ankle area of the foot 10. The support shank 30 is typically a block-configured structure, although it is not limited to such configuration. Preferably, the support shank 30 is comprised of a substantially rigid and durable material. The support shank 30 includes means for attachment to the limb-engaging member (not shown), such as the illustrated groove 32 which would removably receive a tongue of the limb engaging member.

A first spring 34 extends downwardly from a front portion of the support shank 30 to a connection point 36 at the first toe platform 24. A second pair of springs 38 and 40 extend in parallel relation to one another from a back end of the support shank 30 to connection points 42 and 44 at a forward end of the second platform 26, defining a mid-section platform area. A third spring 46 extends from a front portion of the support shank 30 to a connection point 48 at a rear end of the second platform 26, defining a heel platform area. The third spring 46 is disposed between the second springs 38 and 40 so that it can move between the springs 38 and 40 in response to forces applied to the foot 10. The springs 34, 38, 40 and 46 are preferably curvilinear leaf springs, as illustrated. The springs 34, 38, 40 and 46 are preferably comprised of a carbon composite laminate, but may be comprised of other materials, such as titanium or any other suitable material having sufficient resiliency and durable spring characteristics. Many materials are simply not acceptable as the material is too stiff and subject to breakage or failing to provide sufficient bend. Other materials are incapable of supporting the hundreds of pounds of load repeatedly over the course of weeks, months, and even years. In fact, the material used for the springs 34, 38, 40 and 46 must be capable of being subjected to such forces millions of times during their operating life cycle.

It is well-known that a normal gait of a foot is to place the heel, push off or rotate from the outer heel portion across the foot and onto the big toe while the individual's weight is transferred in a forward motion during walking or running. The spring structure of the prosthetic foot 10 of the present invention accommodates this natural fluid movement. The third spring 46 is tensioned as the weight is placed on the heel portion of the foot. As the weight is distributed, this energy is transferred to the second set of springs 38 and 40. Lastly, the force is applied and transferred to the first spring 34 as the weight is transferred to the toe portion of the foot. The hinge 28 allows flexing between the first and second platforms 24 and 26, similar to the ball of the foot pivoting in response to the weight being transferred to the big toe. The result is the elimination of any flat or dead spots, and a very fluid and natural gait.

Figure 3:
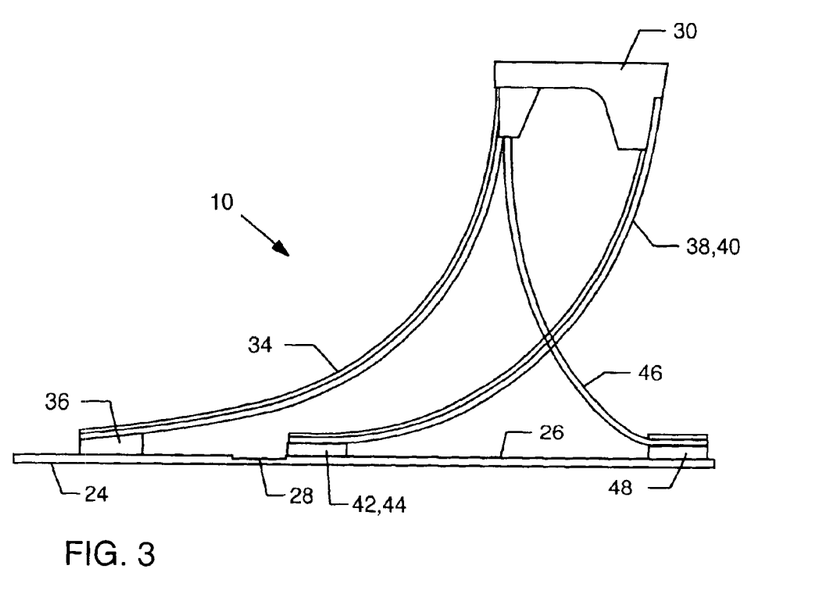
FIG. 3 is a side elevational view of the device of FIG. 2 in an at rest position.
Figure 4:
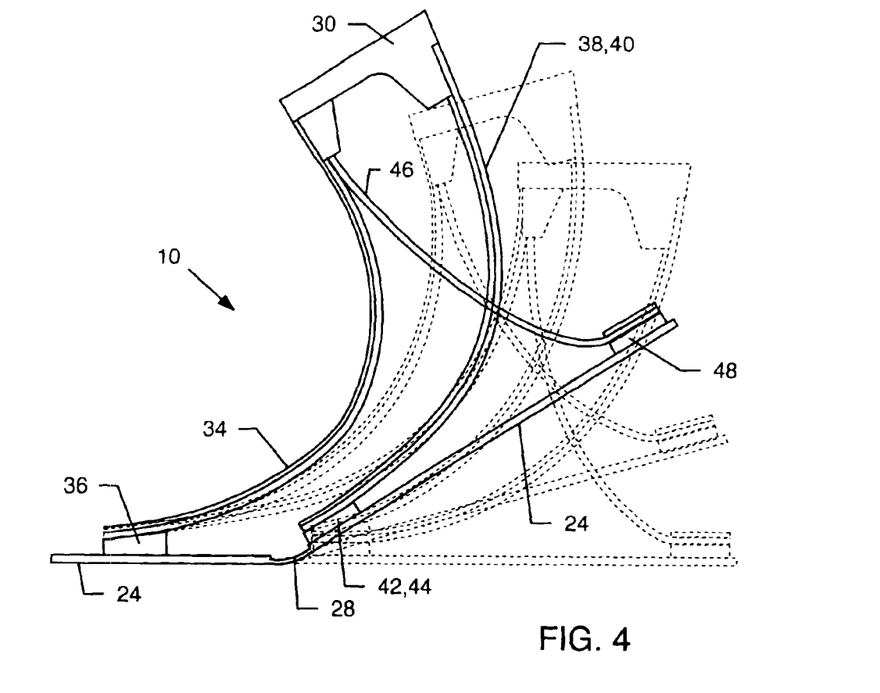
FIG. 4 is a side elevational view similar to FIG. 3, illustrating the device in motion as forces are applied thereto; such as by walking.

With reference now to FIGS. 3 and 4, when at rest, such as when standing on a flat surface, the prosthetic foot device 10 is generally configured as shown in FIG. 3. However, upon walking or running, force is applied at the heel portion 48 to cause spring 46 to bend in reaction to the forces applied thereto. As the heel 48 is lifted, the force is transferred to the mid-section area of the foot 42 and 44 causing springs 38 and 40 to bend in response to the force applied thereto. Springs 38 and 40 respond by pushing against such force and lifting the heel in mid-section area of the foot upwardly. This causes the platform or base 20 to pivot at the hinge section 28 and roll to the toe portion 36. This loads spring 34 causing it to release its energy and push the toe forward and assist the user in lifting the foot 10 off of the ground. Those skilled in the art will know that the flexible base 20, particularly hinge section 28, allow the platforms 36, 42, 44 and 48 to move in a more fluid and natural manner similar to a natural foot in response to these forces.

Figure 5:
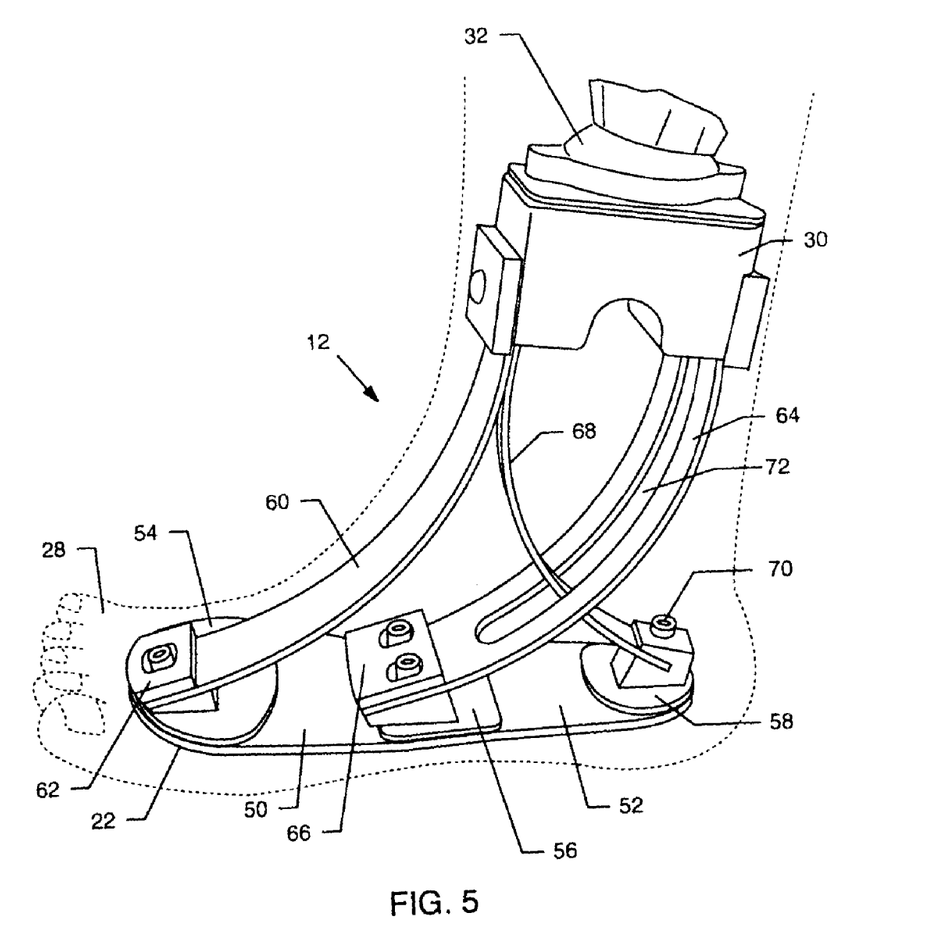
FIG. 5 is a side perspective view of another prosthetic foot device within an encasement, illustrated in phantom.
Figure 6:
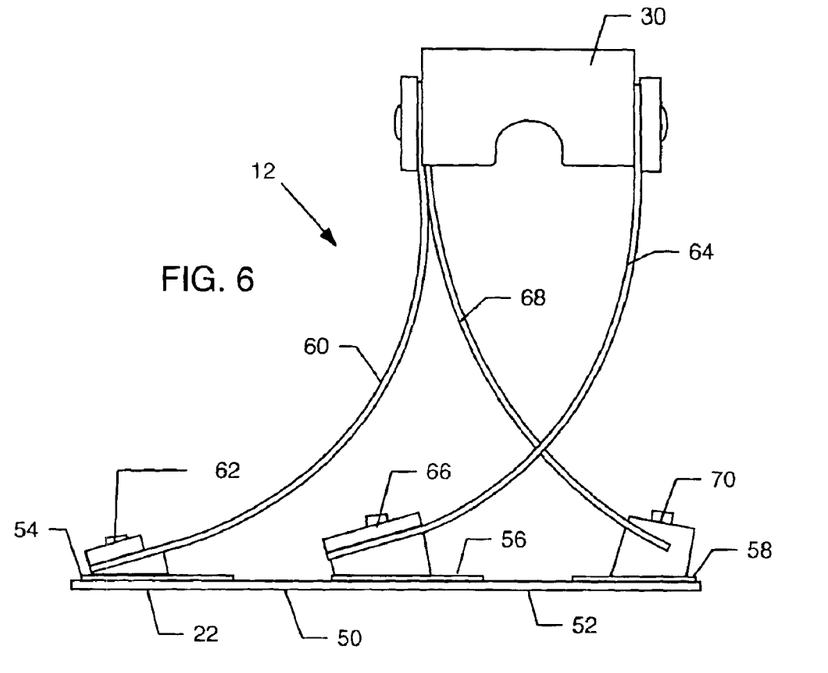
FIG. 6 is a side elevational view of the device of FIG. 5 in an at rest position.

With reference now to FIG. 5, another embodiment of the foot prosthetic 12 is illustrated. Whereas the embodiment illustrated in FIGS. 1 and 2 has a single hinge 28, the embodiment of FIG. 5 has two hinges 50 and 52 formed by the resiliently flexible foot bed which extends between three platforms, namely a toe platform 54, a mid-section platform 56 and a heel platform 58 which are substantially aligned with one another and preferably comprised of a rigid material. The first spring 60 extends from a forward portion of the support shank 30 to a connection point 62 on the toe platform 54 similar to the previous embodiment. However, a single second spring 64 extends from a rear portion of the support shank to a connection point 66 on the mid-section platform. The third spring 68 extends from a forward portion of the support shank 30 to a connection point 70 at the heel platform 58, and extends through an elongated slot 72 formed in the second spring 64. This allows the third spring 68 to at least partly travel the length of the slot 72 in response to forces applied to the foot 12, and particularly to the heel platform 58 in response to walking and running and the like.

Figure 7:
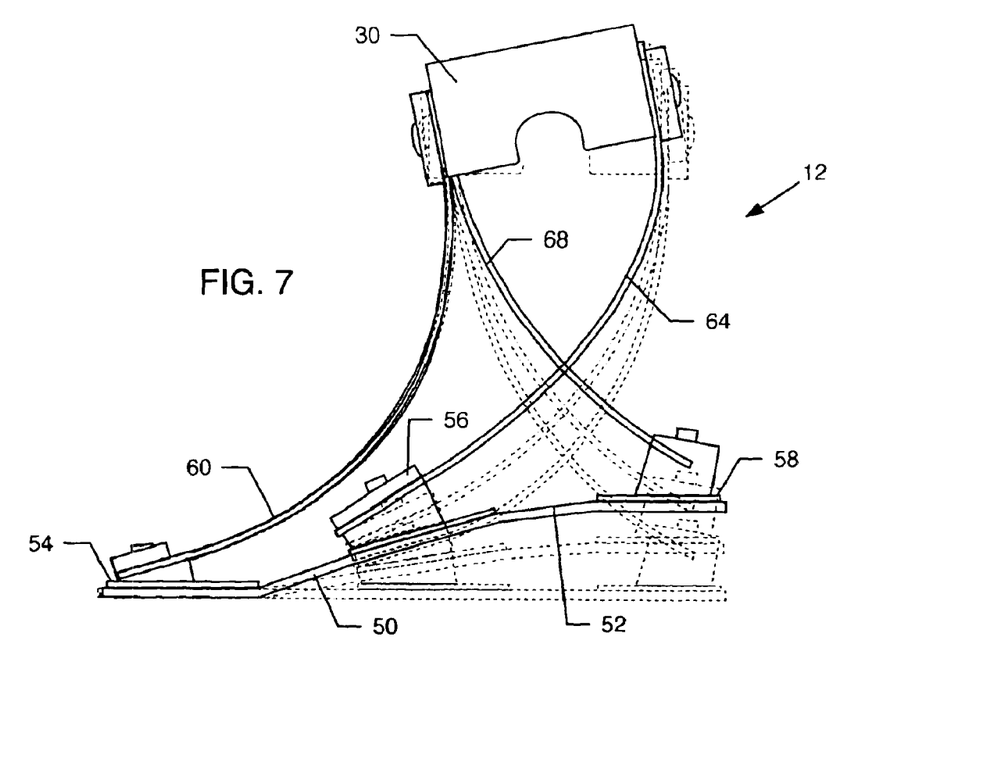
FIG. 7 is a side elevational view similar to FIG. 6, illustrating the device in motion as forces are applied thereto, such as when walking.

With reference now to FIGS. 6–9, when standing on the prosthetic foot 12 on a flat surface, the foot 12 is generally configured as shown. However, upon walking or running, force is applied at the heel portion, and specifically the heel platform 58 so as to cause spring 68 to bend in reaction to the forces applied thereto. As the heel is lifted, the force is transferred to the mid section area of the foot, and in particular to the mid-section platform 56, causing spring 64 to bend in response to the force applied thereto. Springs 64 and 68 respond by pushing against such force and lifting the heel and mid-section area of the foot upwardly. This causes the foot 12 to roll to the toe portion, and in particular to the toe platform 54. This loads spring 60 causing it to release its energy and push the toe forward and assist the user in lifting the foot 12 off of the ground. It will be noted, as illustrated in FIG. 7, that the flexible hinges 50 and 52 allow the platforms 54, 56 and 58 to move in a more fluid and natural manner similar to a natural foot in response to these forces.

Figure 8:
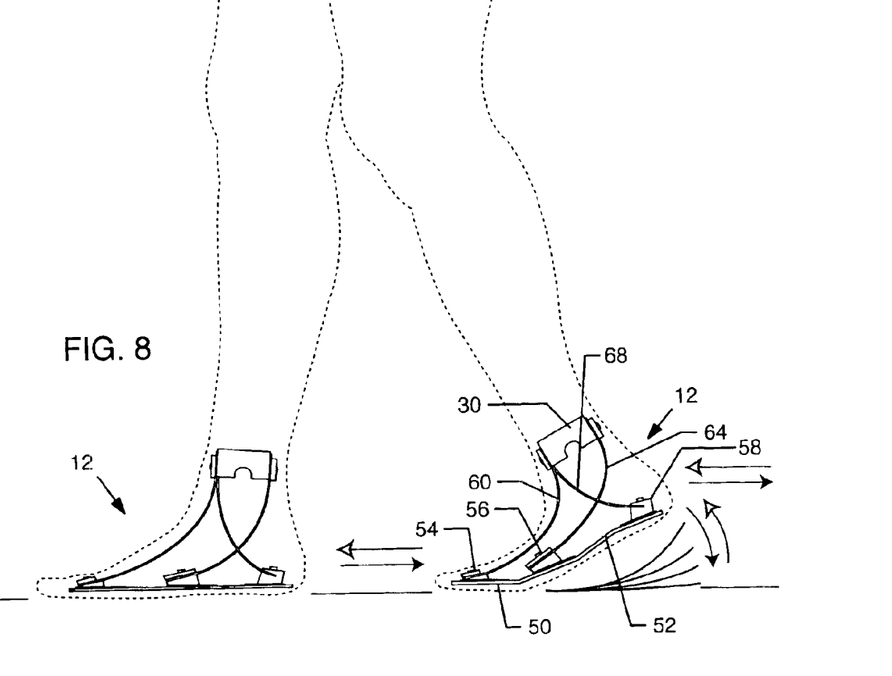
FIG. 8 is a diagrammatic view of the prosthetic foot devices of the present invention, illustrating movement thereof when walking forward or backward.

With particular reference to FIG. 8, a representative drawing is shown with a forward right foot placed on a flat surface and planted for bearing weight. The configuration of the various components of the prosthetic foot 12 are similar to that shown in FIG. 6. The trailing left foot 12 is also shown as it would appear walking forward or backward. The hinges 50 and 52 flex in response to the forces applied to the platforms 54–58. The springs 60, 64 and 68 flex in response to loads applied thereto and release such force independent of one another. Thus, there are no dead or flat spots due to the overloading of the spring. Walking backwards with prior prosthetic feet has been very difficult and unnatural. However, with the prosthetic foot of the present invention, the fluid motion can be achieved with the backwards walking motion as well as the forward walking motion. The forces are merely reversed such that the toe platform 54 and spring 60 are loaded with force first, and then this force is transferred through the mid-section platform 56 and spring 64, and finally the heel platform 58 and spring 68. The one or more hinges created by the resiliently flexible foot bed 22 extending between the platforms provides the pivoting, joint motion which is typical in the ball of the foot adjacent to the toe portion. It will be noted by those skilled in the art that there are no mechanisms designed to imitate the ankle joint. Instead, the springs 60, 64 and 68 serve the purposes of the various muscles, tendons and joints within a real ankle.

Figure 9:
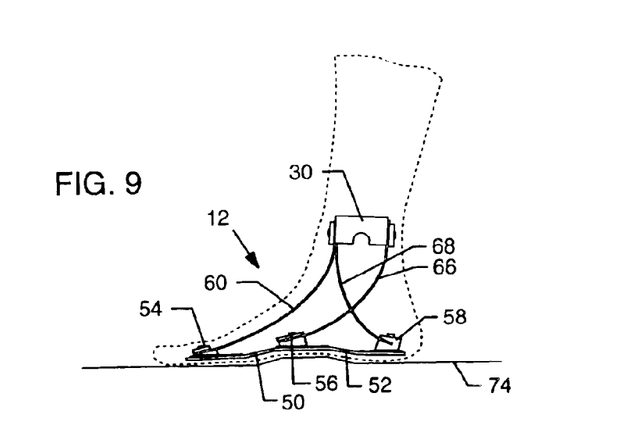
FIG. 9 is a diagrammatic view of the prosthetic foot device at rest on an irregular surface.

With particular reference now to FIG. 9, a prosthetic foot 12 of the present invention is shown on an irregular surface 74. The flexible foot bed 22 allows the spacing between the platforms to flex in a hinged manner and cause the platforms 54–58 to conform to the irregular surface 74, thus providing stable support for the user of the prosthetic foot 12. The inventor is not aware of any prior art prosthetic feet which are capable of conforming to such irregular surfaces.

Figure 10:
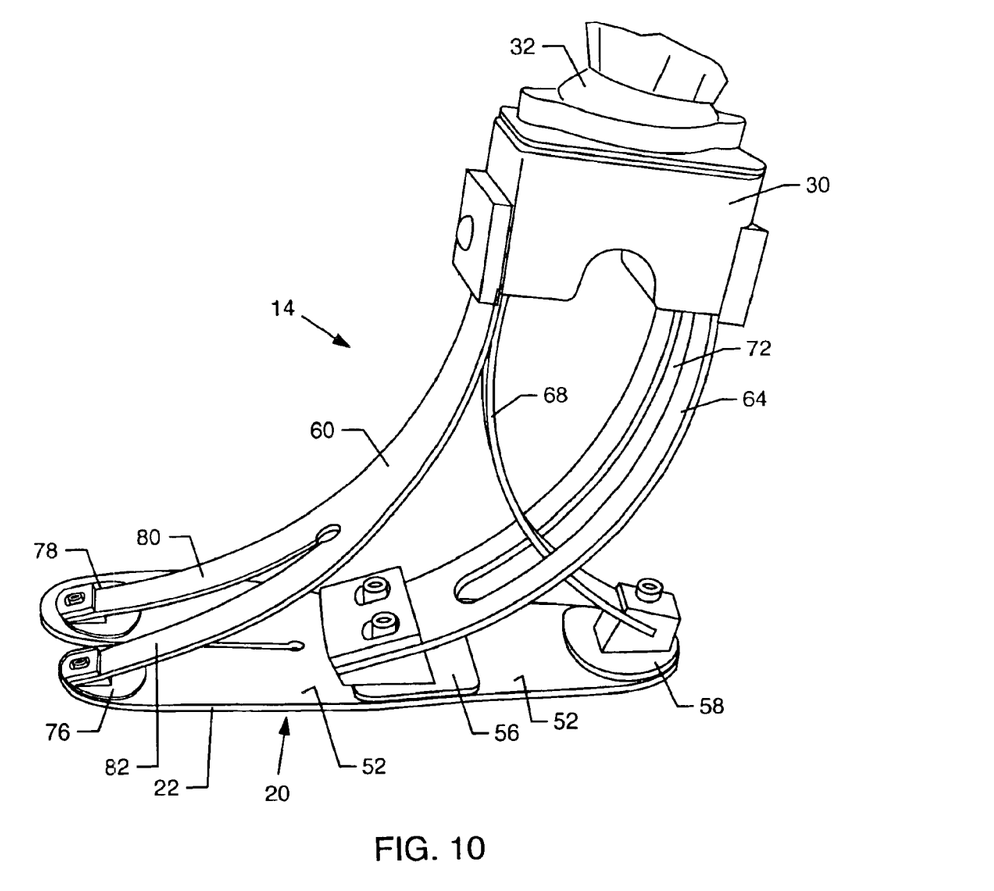
FIG. 10 is a side perspective view of another embodiment of the prosthetic foot device of the present invention.
Figure 11:
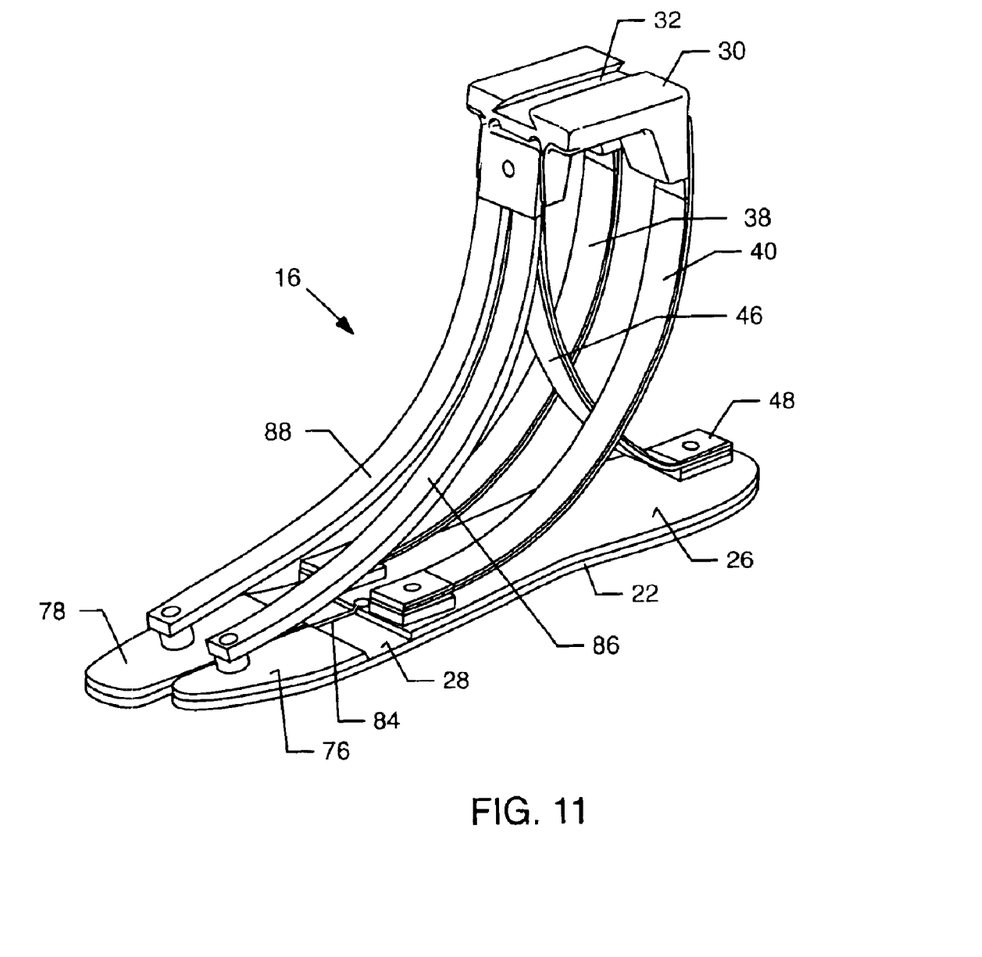
FIG. 11 is a front perspective view of yet another embodiment of the prosthetic foot device of the present invention.

With reference now to FIGS. 10 and 11, as discussed above, the natural gait of a real foot is an outer heel plant, followed by transfer of weight and forces across the mid-section, toes and eventually to the large toe. Thus, the invention contemplates the use of multiple toe platforms 76 and 78 which would mimic the smaller toes and the big toe of a natural foot. With reference to FIG. 8, the first spring 60 could be forked so as to have two ends 80 and 82 which extend to each toe platform 76 and 78. The invention further contemplates a slit 84 formed in the resiliently flexible foot bed 22 to enable the toe platforms 76 and 78 to freely move with respect to one another. However, such slit 84 is not necessary as there would be a degree of freedom of movement between the toe platform 76 and 78 without such slit.

With particular reference to FIG. 11, instead of a forked end, the front spring could comprise two separate springs 86 and 88 which extend from the support shank 30 to the toe platforms 76 and 78 such that each toe platform 76 or 78 as it has force applied thereto directly applies this force to a separate spring 86 or 88.

It will be appreciated by those skilled in the art that the present invention is simple in design, lightweight, and relatively inexpensive to produce. The use of two or more platforms connected to one another with a flexible material, as well as the use of the independent springs or pairs of springs, enable the foot 10–16 to move in a very fluid and natural manner. The prosthetic foot 10–16 of the present invention also enables users to navigate inclines, declines, irregular surfaces, and walk backwards. Navigation of stairs is much more natural as there are no dead or flat spots in the springs as each spring operates independently and is tensioned and released in concert with the other springs to create the fluid movement of the prosthetic foot 10–16. Similarly, the prosthetic foot 10–16 can be used in a more natural manner while riding a bike. This occurs by allowing the toe portion to be put into a "toe cage" of the pedal. The flexibility and hinge-like characteristics of the base 20 allow the toe portion of the foot to be bent in response to the forces applied to the pedal throughout its cyclical motion. Prior art prosthetic feet do not allow such motion and render the riding of a bike very unnatural and cumbersome.

Although several embodiments have been described in detail for purposes of illustration, various modifications may be made without departing from the scope and spirit of the invention. Accordingly, the invention is not to be limited, except as by the appended claims.

What is claimed is:

1. A prosthetic foot, comprising:
   a ground-engaging base having a toe platform, a mid-section platform and a heel platform;
   a flexible hinge extending between the toe and mid-section platforms;
   a first spring extending from the toe platform to a support shank, wherein the support shank is disposed above the platforms so as to be generally positioned above an ankle area of the foot;
   a second spring extending from the support shank to the mid-section platform; and
   a third spring extending from the support shank to the heel platform.

2. The prosthetic foot of claim 1, wherein the platforms are spaced apart and generally aligned with one another.

3. The prosthetic foot of claim 1, including a second flexible hinge extending between the mid-section and heel platforms.

4. The prosthetic foot of claim 3, wherein the flexible hinges comprise a foot bed extending between lower surfaces of the platforms.

5. The prosthetic foot of claim 4, wherein the foot bed is resiliently flexible.

6. The prosthetic foot of claim 4, wherein the foot bed is generally planar.

7. The prosthetic foot of claim 1, wherein the first spring extends from a front portion of the support shank to the toe platform.

8. The prosthetic foot of claim 1, wherein the second spring extends from a back portion of the support shank to the mid-section platform.

9. The prosthetic foot of claim 1, wherein the third spring extends from a front portion of the support shank to the heel platform.

10. The prosthetic foot of claim 1, wherein the first, second and third springs comprise curvilinear leaf springs.

11. The prosthetic foot of claim 10, wherein the second curvilinear leaf spring includes an elongated slot adapted to receive the third curvilinear spring therethrough so as to permit the third curvilinear spring to travel along at least a partial length of the second curvilinear spring in response to forces applied to the prosthetic foot.

12. The prosthetic foot of claim 10, wherein the first curvilinear spring includes a forked end defining two ends, the ends being attached to laterally spaced apart toe platforms.

13. The prosthetic foot of claim 12, wherein the flexible hinge comprises a generally planar and resiliently flexible foot bed extending between lower surfaces of the platforms, and wherein the foot bed includes a slit between the laterally spaced apart toe platforms.

14. The prosthetic foot of claim 1, wherein the second spring comprises a pair of springs extending from the support shank to a pair of mid-section platforms, each second spring being disposed on opposite sides of the third spring.

15. The prosthetic foot of claim 1, wherein the first spring comprises a pair of springs, each spring extending from the support shank to a pair of laterally spaced apart toe platforms.

16. The prosthetic foot of claim 15, wherein the flexible hinge comprises a generally planar and resiliently flexible foot bed extending between lower surfaces of the platforms, and wherein the foot bed includes a slit between the laterally spaced apart toe platforms.

17. The prosthetic foot of claim 1, wherein the platforms are substantially rigid.

18. The prosthetic foot of claim 1, wherein the mid-section platform is defined by a forward portion and the heel platform is defined by a rear portion of a unitary platform.

19. A prosthetic foot, comprising:
    a ground-engaging base having generally aligned and spaced apart toe, mid-section and heel platforms;
    flexible hinges extending between the platforms;
    a first curvilinear spring extending from the toe platform to a support shank disposed above the platforms so the support shank is positioned generally above an ankle area of the foot;
    a second curvilinear spring extending from the mid-section platform to the support shank; and
    a third curvilinear spring extending from the heel platform to the support shank.

20. The prosthetic foot of claim 19, wherein the flexible hinges comprise a generally planar and resiliently flexible foot bed extending between lower surfaces of the platforms.

21. The prosthetic foot of claim 19, wherein the first spring extends from a front portion of the support shank to the toe platform, wherein the second spring extends from a back portion of the support shank to the mid-section platform, and wherein the third spring extends from a front portion of the support shank to the heel platform.

22. The prosthetic foot of claim 19, wherein the second curvilinear spring includes an elongated slot adapted to receive the third curvilinear spring therethrough so as to permit the third curvilinear spring to travel along at least a partial length of the second curvilinear spring in response to forces applied to the prosthetic foot.

23. The prosthetic foot of claim 19, wherein the second spring comprises a pair of springs extending from the support shank to a pair of mid-section platforms, each second spring being disposed on opposite sides of the third spring.

24. The prosthetic foot of claim 19, wherein the first spring includes a forked end defining two ends, each end being attached to laterally spaced apart toe platforms.

25. The prosthetic foot of claim 24, wherein the flexible hinges comprise a generally planar and resiliently flexible foot bed extending between lower surfaces of the platforms, and wherein the foot bed includes a slit between the laterally spaced apart toe platforms.

26. A prosthetic foot, comprising:
    a ground-engaging base having generally aligned and spaced apart first and second platforms, the first platform defining a toe platform and the second platform defining a mid-section platform at a forward portion thereof and a heel platform at a rearward portion thereof;
    a flexible hinge extending between the first and second platforms;
    a first curvilinear spring extending from the toe platform to a support shank disposed above the platforms so the support shank is positioned generally above an ankle area of the foot;

a second curvilinear spring extending from the mid-section platform to the support shank; and a third curvilinear spring extending from the heel platform to the support shank.

27. The prosthetic foot of claim 26, wherein the flexible hinge comprises a generally planar and resiliently flexible foot bed extending between lower surfaces of the platforms.

28. The prosthetic foot of claim 26, wherein the first spring extends from a front portion of the support shank to the toe platform, wherein the second spring extends from a back portion of the support shank to the mid-section platform, and wherein the third spring extends from a front portion of the support shank to the heel platform.

29. The prosthetic foot of claim 26, wherein the second curvilinear spring includes an elongated slot adapted to receive the third curvilinear spring therethrough so as to permit the third curvilinear spring to travel along at least a partial length of the second curvilinear spring in response to forces applied to the prosthetic foot.

30. The prosthetic foot of claim 26, wherein the second spring comprises a pair of springs extending from the support shank to a pair of mid-section platforms, each second spring being disposed on opposite sides of the third spring.

31. The prosthetic foot of claim 26, wherein the first spring includes a forked end defining two ends, each end being attached to laterally spaced apart toe platforms.

32. The prosthetic foot of claim 31, wherein the flexible hinge comprises a generally planar and resiliently flexible foot bed extending between lower surfaces of the platforms, and wherein the foot bed includes a slit between the laterally spaced apart toe platforms.

* * * * *